United States Patent [19]

De Buck

[11] Patent Number: 5,350,301
[45] Date of Patent: Sep. 27, 1994

[54] METHOD AND APPARATUS FOR APPLYING A DIRECTION-ADJUSTING EXTENSION PIECE IN A DENTAL IMPLANT

[75] Inventor: Vincent De Buck, Sint-Niklaas, Belgium

[73] Assignee: Alphadent, Antwerpen, Belgium

[21] Appl. No.: 108,796

[22] Filed: Aug. 19, 1993

[30] Foreign Application Priority Data

Aug. 19, 1992 [BE] Belgium .............................. 09200726

[51] Int. Cl.⁵ .............................................. A61C 8/00
[52] U.S. Cl. ......................................... 433/173; 433/72
[58] Field of Search ................. 433/72, 75, 76, 172, 433/173, 174, 175, 176

[56] References Cited

U.S. PATENT DOCUMENTS

| | | |
|---|---|---|
| 4,187,609 | 2/1980 | Edelman .............................. 433/176 |
| 4,734,035 | 3/1988 | Cheng et al. ........................ 433/72 |
| 5,018,970 | 5/1991 | Stordahl ............................... 433/75 |
| 5,030,095 | 7/1991 | Niznick ................................ 433/174 |
| 5,215,460 | 6/1993 | Perry .................................... 433/75 |

FOREIGN PATENT DOCUMENTS

| | | | |
|---|---|---|---|
| 0198306 | 10/1986 | European Pat. Off. ............ 433/173 |
| 0313222 | 4/1989 | European Pat. Off. ............ 433/173 |
| 9209242 | 6/1992 | World Int. Prop. O. .......... 433/173 |

*Primary Examiner*—John J. Wilson
*Attorney, Agent, or Firm*—Bacon & Thomas

[57] ABSTRACT

A method for applying a direction-adjusting extension piece in a dental implant includes the steps of screwing an orientation axle, provided with marks, in an implant; determining the required axis adjustment; screwing the orientation axle out of the implant, and screwing in an appropriate extension piece, with the determined necessary axis correction. The invention is also directed to the various components used in this method.

18 Claims, 3 Drawing Sheets

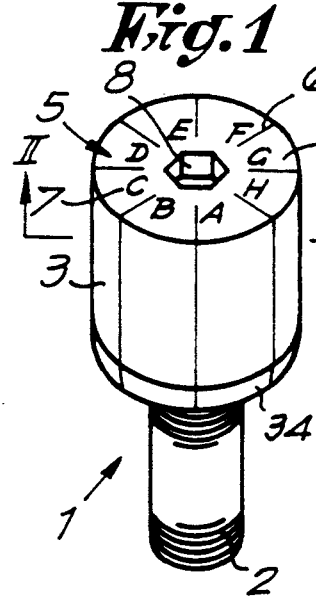
Fig.1
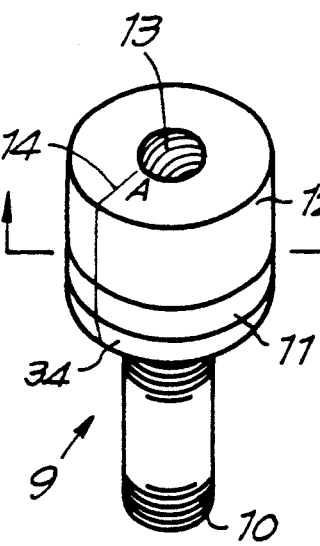
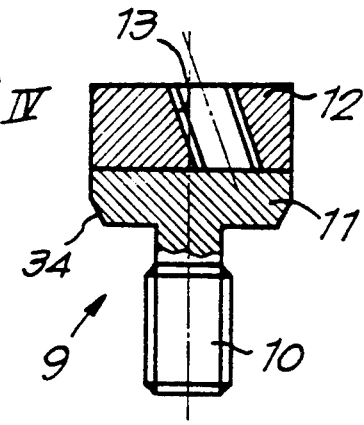
Fig.4
Fig.3
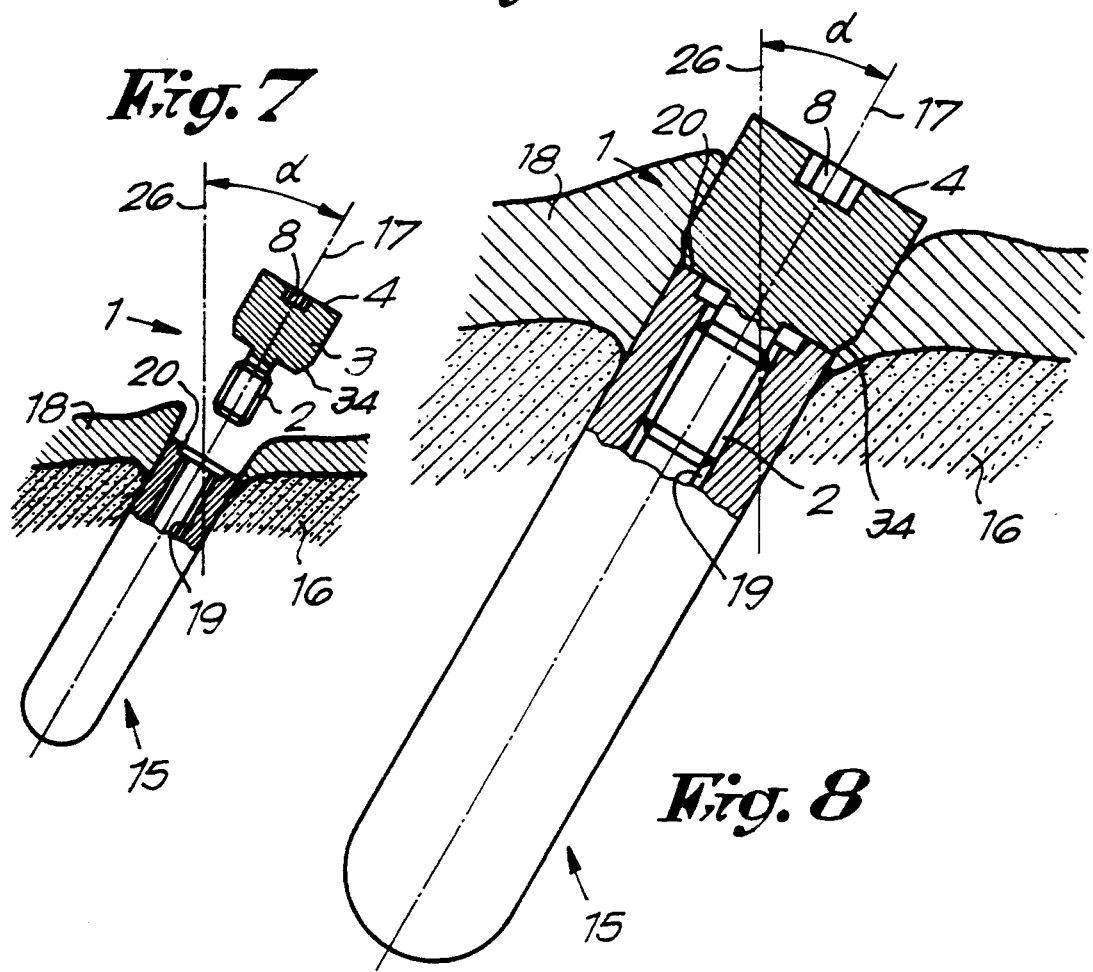
Fig.7
Fig.8

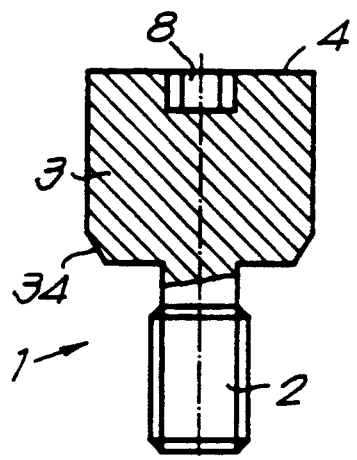
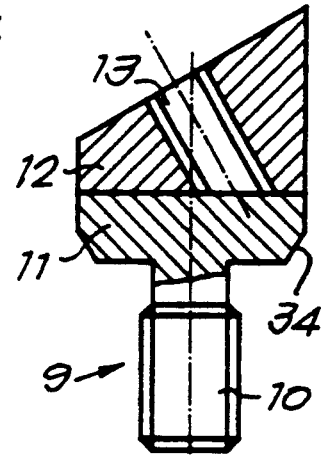
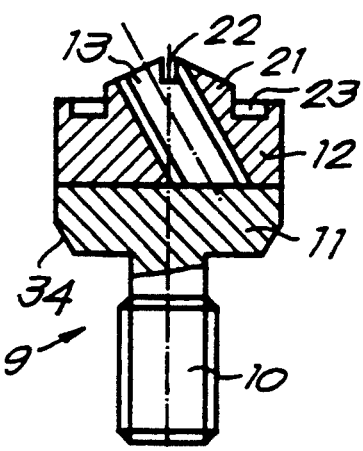
Fig. 2  Fig. 5  Fig. 6
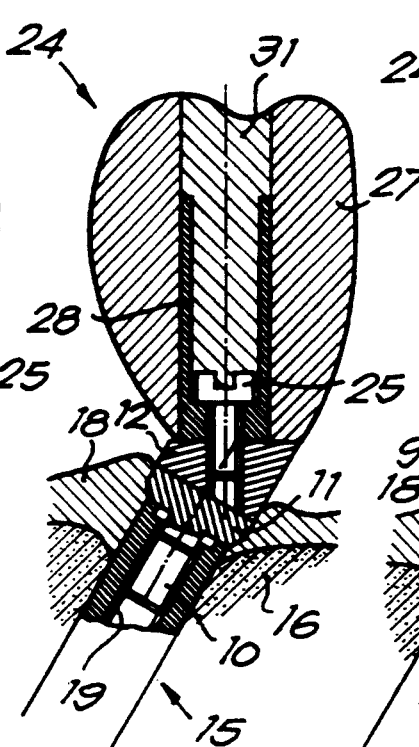
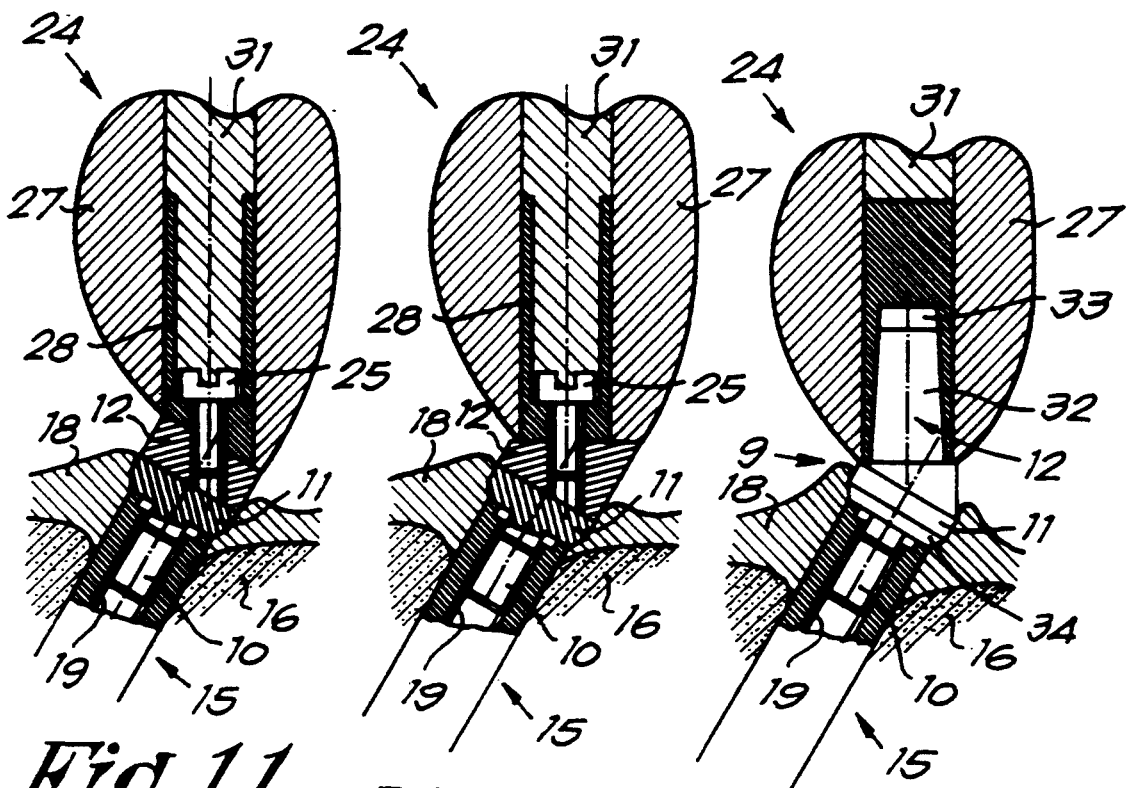
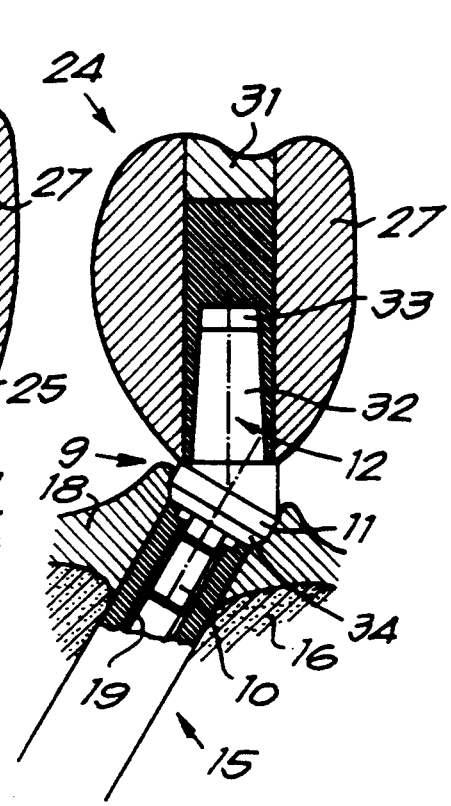
Fig. 11  Fig. 12  Fig. 13

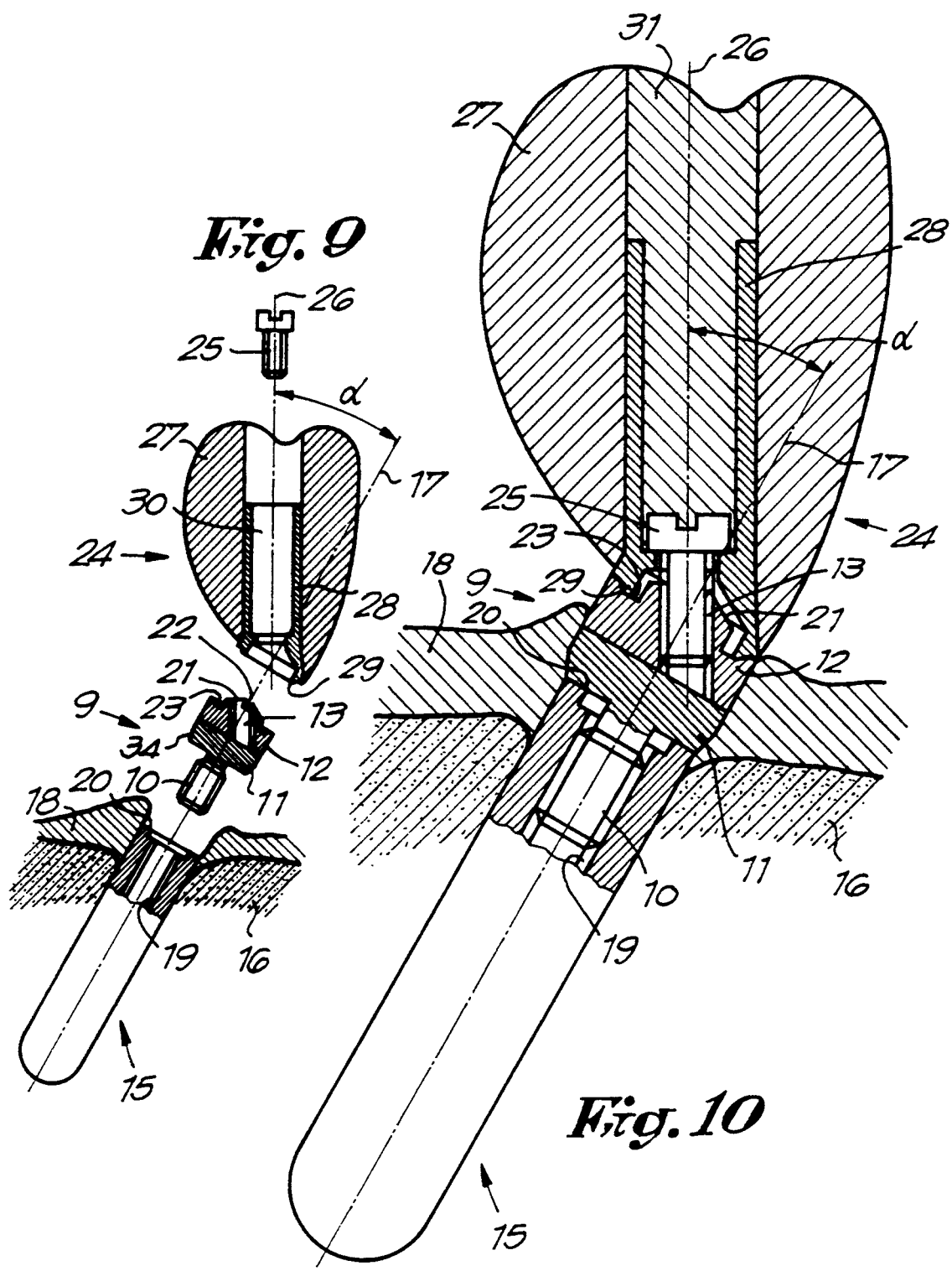

METHOD AND APPARATUS FOR APPLYING A DIRECTION-ADJUSTING EXTENSION PIECE IN A DENTAL IMPLANT

BACKGROUND OF THE INVENTION

This invention relates to a method for applying a direction-adjusting extension piece in dental implants and to the elements used thereby.

It is known that in dental prosthetics methods exist for permanently connecting dentures to a completely or partially toothless jaw.

The known methods for fixedly connecting dentures to a toothless jaw can, among other things, exist in implanting, after opening the mucosa or mucous membrane, of a cylindrical structure from a bio-compatible material, for instance titanium, in the bone of the upper or lower jaw, whereby this cylinder-shaped structure is completely countersunk in the bone, after which the mucosa or mucous membrane is sewn up and a waiting period of approximately six months is required, in order to allow the bone to grow together, osseo-integrate respectively, with the implanted structure.

After this waiting period, the mucosa or mucous membrane is re-opened at the implant, and a temporary extension piece is screwed in the implant, after which the mucous membrane is sewn up again around this temporary extension piece. Such a temporary extension piece is used for obtaining, during the healing process of the mucous membrane, a correct transmucosal diameter.

After the mucous membrane has healed, the temporary extension piece is replaced with a definitive extension piece with the required length.

Both the temporary and the definitive extension pieces are screwed in along the axis of the implant.

The definitive extension piece is provided occlusally with internal screw threads upon which the proper dentures can be screwed in the direction of the axis of the implant.

The success level of such an osseo-integration is very high and has been accepted scientifically and clinically.

Depending on the quality of the bone, several implants can be applied, thus enabling a bridge structure, for instance in the form of a tooth ring, to be screwed in. In this tooth ring, small holes are provided through which a prosthesis screw is applied for connecting the tooth ring to each implant.

The above applied prosthesis screws are usually screwed tight in the direction of the axis of the extension piece, so that the axis direction of the implant determines the axis direction of the extension piece and thus also the axis direction of the tooth placed thereupon with the prosthesis screw.

The bone quality, the bone volume and the anatomic limitations of the lower and especially upper jaw sometimes force the surgeon to place the implant at a location not corresponding to the natural location of the former tooth position, thus causing afterwards functional, hygienic and aesthetic complications in the prosthetic field.

If the axis direction of the implant is unfavorable, the access for the screw is provided at unwanted places, and the axis direction of the connected dentures will also be unfavorable, thus causing aesthetic problems.

In order to adjust the axis direction of such unfavorably orientated implants, several direction-adjusting extension pieces have been previously proposed.

Among other things, pre-formed and inclined extension pieces are known, which are glued in the implant, having as a disadvantage, however, that a permanent connection is obtained.

Moreover, the height of such inclined extension pieces often causes aesthetic problems.

Also, bendable extension pieces with a thin neck are known, which can be screwed in the implant, however, they have been found to break easily.

Furthermore, deformable or grindable synthetic extension pieces are known, which are cast in metal through a lost wax casting technique, so that an individual extension piece is obtained, which is breakable, however, and usually fits badly in the implant. Moreover, this method is time-consuming and the extension pieces are not reproduceable if a replacement is necessary.

Other known extension pieces are provided with a ball joint which can be locked. These extension pieces present the disadvantage that they are very complex and very breakable due to their small dimensions.

With the known extension pieces the screw thread of the implant has to be reproduced on a working model with printing systems in order to manufacture an individual extension piece, which is also time-consuming, cumbrous and inaccurate due to the lack of visual control.

SUMMARY OF THE INVENTION

The present invention aims at a method and elements used thereby which provide a solution for applying direction-adjusting extension pieces.

To this end, the invention relates to a method for applying a direction-adjusting extension piece in a dental implant, which mainly consists in screwing an orientation axle, provided with marks, in an implant; determining the required axis correction; screwing the orientation axle out and screwing a direction-adjusting extension piece in the implant, thus obtaining the necessary axis adjustment.

The elements which are used with this method include, on the one hand, an orientation axle with marks and, on the other hand, a series of direction-adjusting extension pieces which allow consecutively an axis correction according to one of the marks on the orientation axle.

BRIEF DESCRIPTION OF THE DRAWINGS

In order to better show the characteristics of the invention, some preferred embodiments are described hereafter, as examples without any limiting character, reference being made to the accompanying drawings, in which:

FIG. 1 shows a schematic representation of an orientation axle according to the invention in perspective;

FIG. 2 represents a cross-section according to line II—II in FIG. 1;

FIG. 3 is a schematic representation of a direction-adjusting extension piece according to the invention;

FIG. 4 represents a cross-section according to line IV—IV in FIG. 3;

FIGS. 5 and 6 represent cross-sections similar to that of FIG. 4, but for different embodiments;

FIG. 7 represents a cross-section in an exploded view of a dental implant with an orientation axle according to the invention;

FIG. 8 represents a cross-section to a larger scale of an orientation axle mounted in a dental implant;

FIG. 9 represents a cross-section in an exploded view of a dental implant and a direction-adjusting extension piece with supra-structure;

FIG. 10 represents a cross-section to a larger scale of a direction-adjusting extension piece mounted in a dental implant, and of the corresponding supra-structure;

FIG. 11 represents a view similar to that of FIG. 10, in which the direction-adjusting extension piece according to FIG. 4 is used;

FIG. 12 represents a view similar to that of FIG. 10, in which the direction-adjusting extension piece according to FIG. 5 is used;

FIG. 13 represents a view similar to that of FIG. 10, in which yet another direction-adjusting extension piece is used.

DETAILED DESCRIPTION OF THE PREFERRED EMBODIMENTS

In the method according to the invention, use is made, among other things, of an orientation axle 1 as represented schematically in FIG. 1 which consists of, on the one hand, a screw thread part 2, and, on the other hand, of a cylindrical body 3 with flat top 4 on which marks 5 are provided.

In a preferred embodiment, these marks 5 consist of radial stripes 6 applied to the flat top 4 with a corresponding identification element 7, such as for instance numbers or letters, in this case the letters A to H.

The flat top 4 can be provided with a hole 8, for instance a hexagon, to facilitate the screwing in and out of the orientation axle.

For convenience's sake, the marks 6 can be continued on the circumference of the cylindrical body 3.

FIGS. 3 and 4 represent a schematic view of a first direction-adjusting extension piece 9 according to the invention, which is used with the method according to the invention.

This extension piece 9 consists of, on the one hand, a screw thread part 10 which is identical to the screw thread part 2 of the orientation axle 1, on which a head 11 is provided, and, on the other hand, of a proper direction-adjusting element 12 connected to this head 11, which is provided with a screw thread 13 directed aslant in relation to the axis of the extension piece 9.

The direction-adjusting element 12 is provided at its upper surface with a mark 14 which can correspond to one of the marks 5 of the orientation axle 1 and which is preferably provided in a similar manner with an indication, in this case the indication A, which implies that this extension piece corresponds to a correction mark A of the orientation axle 1.

FIG. 5 represents a direction-adjusting extension piece, which merely differs from the extension piece in FIG. 4 in that its upper surface is directed aslant, more specifically at right angles to the heart line of the screw thread 13.

FIG. 6 represents a direction-adjusting extension piece which will be discussed in further detail hereafter.

The manufacturing of these elements, namely the orientation axle 1 and the extensions pieces 9 is done as follows.

The orientation axle 1 can be formed automatically in one part. The screw thread part 2 provided at the bottom of the orientation axle 1 is manufactured in such a way that it is in accordance with the inner screw thread of the implant with which it is used.

This orientation axle 1 is screwed in a mother matrix, for instance a plate, up to a fixed stop formed by the lower surface of the body 3 of the orientation axle 1. The mother matrix is provided around the orientation axle 1 screwed therein, with marks, for instance stripes, which can be similarily applied on the orientation axle 1, for instance by means of a laser technique, etching, scratching or the like.

Subsequently, the orientation axle 1 is screwed out of the mother matrix and can be used as such.

The mother matrix is then used for manufacturing the direction-adjusting extension pieces 9.

To that end, the screw thread part 10 of the head 11 is screwed in the mother matrix, more specifically in the screw thread hole in which the orientation axle 1 was screwed, up to a fixed stop formed by the lower surface of head 11.

Subsequently, the proper direction-adjusting element 12 is placed on top of the basic screw thread part 10 and orientated thereupon by placing the mark 14 of element 12 opposite to one of the marks applied in the mother matrix, in this case A to H.

The marks are standardized on the mother matrix and thus also with respect to the coils of the screw thread parts 2 and 10 of the orientation axle 1 and the head 11 respectively.

Both the head 11 and the actual direction-adjusting part 12 of the extension piece 9 are manufactured automatically.

After accurate placing of the part 12 on the head 11, these parts are permanently connected, for instance by means of glueing, soldering or a laser technique, to form the complete extension piece 9, after which this extension piece 9 is screwed out of the mother matrix.

It is clear that the same mother matrix can be used for manufacturing different direction-adjusting extension pieces, whereby the orientation direction of the screw thread passing through aslant is indicated by means of corresponding marks.

Besides the orientation axles 1 having in this case the indications A, B, C, D, E, F, G and H, direction-adjusting extension pieces 9 will be formed, whose axis adjustment corresponds to one of the marks, in other words extension pieces A, B, C, D, E, F, G and H.

The method according to the invention for applying a direction-adjusting extension piece in a dental implant is explained with reference to FIGS. 7, 8, 9 and 10, whereby in FIGS. 9 and 10 the extension piece 9 according to the embodiment of FIG. 6 is used.

FIGS. 7 and 8 are schematic representations of a dental implant 15 which is applied in the bone 16 of the upper or lower jaw and which is already fully integrated therein.

The axis direction 17 of the implant 15, however, differs with an angle α from the axis direction of the natural position of the tooth. Such difference can be caused for instance by inaccurate positioning of the implant 15, due to anatomic limitations or the like.

The bone 16 is covered at the top with the mucosa or mucous membrane 18 which has been opened at the implant 15 so that the end 20 of the implant, provided with internal screw thread 19, can be reached via the mouth.

According to the invention, an orientation axle 1 is subsequently applied in the end 20 of the implant 15, as represented in FIGS. 7 and 8. The screw thread parts 2 and 19 of the orientation axle 1 and the implant 15 are similar to one another and can only be screwed together from a particular position until the lower surface of the cylindrical body 3 of the orientation axle 1 forms a stop against the upper surface of the implant 15. This causes the orientation axle 1 to be in one specific orientation.

This orientation axle 1 can be freely screwed in or out of the implant 15, or even be replaced with an other orientation axle 1, whose marks are also standardized.

With the help of the marks 5 applied on the orientation axle 1, the dentist can then decide which correction of the implantation axis 17 has to be executed and determine the corresponding direction-adjusting extension piece with the help of the marks 5 applied on the orientation axle 1.

Depending on the final position of the orientation axle 1, the dentist will read a mark, for instance A, so that he knows that a corresponding direction-adjusting extension piece A will have to be used.

After the required correction has been determined, the orientation axle 1 is screwed out of the implant and, as represented in FIGS. 9 and 10, replaced by a direction-adjusting extension piece 9, which is screwed in the implant 15 with its screw thread part 10, until the bottom part of the head 11 of this extension piece 9 forms a stop against the implant 15.

The axis correction is therefore automatically obtained since the aslant directed screw thread 13 is directed perpendicularly or almost perpendicularly to the bone 16.

In the embodiment according to FIG. 6, the actual direction-adjusting element 12 is provided with a central part 21 in which for instance a transverse groove 22 is applied allowing for the extension piece 9 to be rotated by means of a fit tool, while around the central part 21 a cylindrical groove 23 is provided, a side edge of which is directed aslant.

In the preferred embodiment, as represented in FIGS. 9 and 10, it is shown that with the thus applied extension piece 9, a supra-structure 24 is connected by means of a prosthesis screw 25 which is screwed in the screw thread 13 of the extension piece 9, so that the axis 26 of the applied supra-structure 24 is identical to the direction previously determined, being the axis direction of the natural direction of the tooth 27.

In this case, the supra-structure 24 consists of a hollow support 28, whose lower extremity has a circumferential rib 29 with a slanting side edge, cooperating with the groove 23 in the extension piece 9 in order to position the hollow support 28 effectively with respect to the extension piece 9.

Naturally, the lower extremity of the hollow support 28 has a slanting structure in this embodiment which can be connected to the extension piece 9.

The actual tooth 27 is maintained on the hollow structure 28, for instance by means of baked porcelain.

When the tooth 27 has been applied and connected with respect to the implant, cavity 30 will eventually be provided with a suitable filling 31.

For the sake of completeness, FIG. 11 represents an embodiment of a supra-structure 24 which is meant to be used with a direction-adjusting extension piece 9 according to the embodiment of FIG. 4, whereas FIG. 12 represents an embodiment whereby the supra-structure 24 cooperates with a direction-adjusting extension piece 9 according to the embodiment represented in FIG. 5.

Finally, FIG. 13 represents a supra-structure 24 which will be used with a direction-adjusting extension piece 9 which is obtained and applied in the same way as described above, and whereby use is made of a conical axle 32 replacing the screw thread 13 and upon which the supra-structure 24 is maintained by clenching the conical hole 33 on the conical axle 32.

It should be noted that both the orientation axle 1 and the direction correcting extension pieces 9 are preferably provided with a slanting edge 34 which facilitates the penetration of these parts in the mucosa or mucous membrane.

The present invention is in no way intended to be limited to the embodiments described as examples and represented in the figures.

I claim:

1. An arrangement for correcting an orientation axis associated with a dental implant comprising: an orientation axle including a screw thread part and a body, said body being provided, at least at an upper extension portion thereof, with a plurality of circumferentially spaced marks; and a series of extension pieces each of which has an associated direction-adjusting element that defines a predetermined mounting axis corresponding to a respective one of said plurality of marks, whereby said orientation axle may be placed within a dental implant to determine a required adjustment of an orientation axis associated with the implant and a respective one of said extension pieces can be selected based on the presence of said plurality of marks.

2. An arrangement according to claim 1, wherein said screw thread part is adapted to be threadably received within an internal screw thread of an implant.

3. An arrangement according to claim 1, wherein the marks continue about the circumference of the body.

4. An arrangement according to claim 1, wherein each mark is formed by a stripe.

5. An arrangement according to claim 1, wherein each mark has an associated identification element.

6. An arrangement according to claim 1, wherein each of said direction-adjusting extension pieces comprises a head, which forms an extension of a screw thread part, and a direction-adjusting part connected to said head.

7. An arrangement according to claim 6, wherein said direction-adjusting part is provided with a screw thread hole which is placed at an angle in relation to a longitudinal axis of the extension piece.

8. An arrangement according to claim 7, wherein the direction-adjusting part is connected to the head thereof by means of gluing.

9. An arrangement according to claim 7, wherein the direction-adjusting part is connected to the head thereof by means of soldering or welding.

10. An arrangement according to claim 7, further comprising a tooth, which is to be connected to the extension piece, mounted on a hollow support in which, after mounting, a filling is applied, said hollow support having an aslant bottom, whereby through the hollow support, a screw can be applied for mounting the tooth to the extension piece by threading the screw into said screw thread hole.

11. An arrangement according to claim 7, further comprising a tooth, which is to be connected to the extension piece, mounted on a hollow support in which, after mounting, a filling is applied, said hollow support having a bottom that is at a right angle to a longitudinal axis of said hollow support, whereby through the hollow support, a screw can be applied for mounting the tooth to the extension piece by threading the screw into said screw thread hole thereof.

12. An arrangement according to claim 6, wherein said direction-adjusting part is provided with a screw thread hole which is placed at an angle in relation to a longitudinal axis associated with the extension piece, whereby an upper wall of the direction-adjusting part defines a plane which is aslant and whereby this plane is directed at right angles to the screw thread hole.

13. An arrangement according to claim 6, wherein an upper wall and the direction-adjusting part is at right angles to a longitudinal axis of the extension piece.

14. An arrangement according to claim 6, wherein said direction-adjusting part is formed by a conical axle which is placed at an angle in relation to a longitudinal axis of the extension piece.

15. An arrangement according to claim 1, further comprising a tooth which is adapted to be connected to the extension piece, said tooth being mounted on a hollow support in which, at a top thereof, a filling is applied, whereby said hollow support has an aslant bottom and is provided with a conical hole that is adapted to be clenched onto a conical axle in order to connect the tooth to the extension piece.

16. An arrangement according to claim 1, further comprising a tooth which is adapted to be connected to the extension piece, said tooth being mounted on a hollow support in which, at a top thereof, a filling is applied, whereby said hollow support terminates, at a onto a conical axis in order to connect the tooth to the extension piece.

17. A method for applying a direction-adjusting extension piece in a dental implant in order to correct an orientation axis associated with the implant comprising: screwing an orientation axle, provided with various circumferentially spaced marks, in an implant having an associate axis oriented in a certain manner; determining a required axis adjustment corresponding to one of said marks; screwing said orientation axle out of the implant; and screwing in one of a series of extension pieces which correspond to said one of said marks so as to provide the necessary axis correction.

18. A method according to claim 17, further comprising constructing each of said extension pieces by starting from an orientation axle which is screwed completely in a screw thread hole of a mother matrix; transferring marks provided on this mother matrix to this orientation axle; screwing the thus completed orientation axle out; screwing a head portion of a direction-adjusting extension piece completely in the same screw thread hole of the same mother matrix; connecting a direction-adjusting part of the extension piece to said head in such a way that a mark on the direction-adjusting part is placed opposite to a corresponding mark of the mother matrix; and repeating this process to form the series of extension pieces such that for each mark of the orientation axle, a different extension piece is obtained.

* * * * *